(12) United States Patent
Wang

(10) Patent No.: US 10,117,624 B2
(45) Date of Patent: Nov. 6, 2018

(54) ELECTRICAL IMPEDANCE DETECTION AND ULTRASOUND SCANNING OF BODY TISSUE

(76) Inventor: Wei Wang, Leicester (GB)

(\*) Notice: Subject to any disclaimer, the term of this patent is extended or adjusted under 35 U.S.C. 154(b) by 1531 days.

(21) Appl. No.: 13/510,762

(22) PCT Filed: Nov. 22, 2010

(86) PCT No.: PCT/EP2010/067951
§ 371 (c)(1),
(2), (4) Date: Oct. 24, 2013

(87) PCT Pub. No.: WO2011/061338
PCT Pub. Date: May 26, 2011

(65) Prior Publication Data
US 2014/0058212 A1 Feb. 27, 2014

(30) Foreign Application Priority Data
Nov. 20, 2009 (GB) .................. 0920388.6

(51) Int. Cl.
*A61B 5/05* (2006.01)
*A61B 5/00* (2006.01)
(Continued)

(52) U.S. Cl.
CPC ............ *A61B 5/743* (2013.01); *A61B 5/0035* (2013.01); *A61B 5/0536* (2013.01); *A61B 8/14* (2013.01);
(Continued)

(58) Field of Classification Search
USPC ........................................................ 600/437
See application file for complete search history.

(56) References Cited

U.S. PATENT DOCUMENTS

| 4,545,385 A | 10/1985 | Pirschel |
| 6,645,144 B1 * | 11/2003 | Wen .................. G01N 29/0609 600/407 |

(Continued)

FOREIGN PATENT DOCUMENTS

| DE | 3224290 | 12/1983 |
| GB | 2449904 | 12/2008 |

OTHER PUBLICATIONS

International Search Report for PCT Application No. PCT/EP2010/067951 dated Jan. 28, 2011.

*Primary Examiner* — Joel F Brutus
(74) *Attorney, Agent, or Firm* — Meyertons, Hood, Kivlin, Kowert & Goetzel, P.C.; Mark R. DeLuca

(57) ABSTRACT

An apparatus for performing electrical impedance detection and ultrasound scanning of body tissue, the apparatus including: an electrode array for performing electrical impedance detection by applying a first electrical signal to the body tissue, receiving an electrical response signal characteristic of the body tissue, and providing a first output signal representative of the electrical response signal; and an ultrasound transducer for performing ultrasound scanning by applying a first ultrasound signal to the body tissue, receiving an ultrasound response signal characteristic of the body tissue, and providing a second output signal representative of the ultrasound response signal, wherein the ultrasound transducer is mounted so as to be moveable during performance of the ultrasound scanning.

20 Claims, 2 Drawing Sheets

(51) Int. Cl.
  *A61B 5/053* (2006.01)
  *A61B 8/00* (2006.01)
  *A61B 8/14* (2006.01)

(52) U.S. Cl.
  CPC ............ *A61B 8/406* (2013.01); *A61B 8/4416* (2013.01); *A61B 8/4461* (2013.01); *A61B 8/463* (2013.01)

(56) References Cited

U.S. PATENT DOCUMENTS

| | | |
|---|---|---|
| 6,856,824 B1 | 2/2005 | Wang et al. |
| 2002/0106681 A1* | 8/2002 | Wexler .................. A61B 5/0536 435/6.11 |
| 2003/0028092 A1* | 2/2003 | Anderson ............ A61B 5/0536 600/409 |
| 2004/0249283 A1 | 12/2004 | Kantorovich et al. |
| 2006/0085049 A1 | 4/2006 | Cory et al. |
| 2008/0183076 A1* | 7/2008 | Witte ................... A61B 5/0093 600/438 |
| 2008/0242979 A1* | 10/2008 | Fisher .................. A61B 6/4233 600/427 |
| 2009/0259128 A1 | 10/2009 | Stribling |
| 2010/0148798 A1 | 6/2010 | Wang et al. |
| 2010/0210950 A1 | 8/2010 | Dunbar et al. |
| 2010/0241022 A1 | 9/2010 | Wang |
| 2010/0268109 A1 | 10/2010 | Wang |
| 2011/0034806 A1 | 2/2011 | Hartov et al. |

* cited by examiner

ELECTRICAL IMPEDANCE DETECTION AND ULTRASOUND SCANNING OF BODY TISSUE

TECHNOLOGICAL FIELD

The invention relates to an apparatus for, and a method of, performing electrical impedance detection and ultrasound scanning of body tissue. The apparatus and method may be used in applications such as medical diagnostics.

BACKGROUND

Electrical impedance detection, as used in Electrical Impedance Mammography (EIM) and Electrical Impedance Imaging (EII), also referred to as Electrical Impedance Tomography (EIT), Electrical Impedance Scanning (EIS) and Applied Potential Tomography (APT), can provide an image of the spatial distribution of electrical impedance inside body tissue. This is attractive as a medical diagnostic tool because it is non-invasive and does not use ionizing radiation as in X-ray tomography or strong, highly uniform magnetic fields as in Magnetic Resonance Imaging (MRI).

Typically a two dimensional or three dimensional array of evenly spaced electrodes is attached to the body tissue about the region of interest. Voltages are applied across pairs of input electrodes, and output electric currents are measured at output electrodes. Alternatively, input electric currents are applied between pairs of input electrodes, and output voltages are measured at output electrodes or between pairs of output electrodes. For example, a very small alternating electric current is applied between one pair of electrodes, and the voltage between all other pairs of electrodes is measured. The process is then repeated with the current applied between a different pair of the electrodes.

The measured values of the voltage depend on the electrical impedance of the body tissue, and from these values an image is constructed of the electrical impedance of the body tissue. By performing a plurality of such measurements, both two dimensional and three dimensional images can be constructed. Spatial variations revealed in electrical impedance images may result from variations in impedance between healthy and non-healthy tissues, variations in impedance between different tissues and organs, or variations in apparent impedance due to anisotropic effects resulting for example from muscle alignment.

Tissue or cellular changes associated with cancer cause significant localized variations in electrical impedance, and electrical impedance images can be used to detect breast carcinomas or other carcinomas.

The electric current or voltage applied to the electrodes may have a broad range of different frequencies. Different morphologies that have insignificant impedance at one frequency may have a more significant variation in impedance at a different frequency. Signals with different frequencies may penetrate the object in different ways. For example, at one frequency a signal may penetrate most significantly through the inside of cells of body tissue (e.g. intro-cellularly) and at another frequency a signal may penetrate most significantly though spaces between cells of body tissue (e.g. extra-cellularly).

Ultrasound scanning typically involves using a hand-held ultrasound probe that includes an array of ultrasound transducers which both transmit ultrasound energy into body tissue to be examined and receive ultrasound energy reflected from the body tissue. To generate ultrasound energy, a driver circuit of a processing unit sends precisely timed electrical signals to the transducers. Part of the ultrasound pulses is reflected in the body tissue under examination and returns to the transducers. The transducers then convert the received ultrasound energy into electrical signals which are amplified and processed to generate an image of the examined region.

Electrical impedance detection can provide diagnostic information about body tissue, whereas ultrasound scanning can provide high resolution imaging of body tissue.

BRIEF SUMMARY

According to various, but not necessarily all, embodiments of the invention there is provided an apparatus for performing electrical impedance detection and ultrasound scanning of body tissue, the apparatus comprising:

an electrode array for performing electrical impedance detection by applying a first electrical signal to the body tissue, receiving an electrical response signal characteristic of the body tissue, and providing a first output signal representative of the electrical response signal; and an ultrasound transducer for performing ultrasound scanning by applying a first ultrasound signal to the body tissue, receiving an ultrasound response signal characteristic of the body tissue, and providing a second output signal representative of the ultrasound response signal, wherein the ultrasound transducer is mounted so as to be moveable during performance of the ultrasound scanning.

According to various, but not necessarily all, embodiments of the invention there is provided a method of performing electrical impedance detection and ultrasound scanning of body tissue, the method comprising:

performing electrical impedance detection with an electrode array by applying a first electrical signal to the body tissue, receiving an electrical response signal characteristic of the body tissue, and providing a first output signal representative of the electrical response signal; and performing ultrasound scanning with an ultrasound transducer by applying a first ultrasound signal to the body tissue, receiving ultrasound response signals characteristic of the body tissue, and providing a second output signal representative of the ultrasound response signals, wherein the ultrasound transducer is moved during the performing of the ultrasound scanning.

At least some embodiments of the invention therefore provide an apparatus and method for detecting both an electrical response signal and an ultrasound signal. The apparatus and method may therefore provide combined electrical impedance detection and ultrasound scanning. By moving the ultrasound transducer with respect to the electrode array, the ultrasound scanning can provide an image of the body tissue on which the electrical impedance detection is performed.

In one embodiment, the ultrasound transducer may be moveable with respect to the apparatus along a path that is fixed relative to a location of the electrode array at which the electrode array is arranged to perform the electrical impedance detection. Likewise, according to the method, during the performing of the ultrasound scanning the ultrasound transducer may be moved along a path that is fixed relative to a location of the electrode array at which the electrode array is arranged to perform the electrical impedance detection. Therefore, a location of the electrode array and a path of the ultrasound transducer have a fixed relationship. By means of such a fixed relationship, the ultrasound response signals and the electrical response signals can have a high degree of spatial correlation, which can assist detection and characterization of features of the body tissue.

The path of the ultrasound transducer may be a loop. This feature enables the apparatus to be compact.

In one embodiment, the electrode array may be mounted on the apparatus so as to be moveable with respect to the apparatus. By moving the electrode array the first electrical signal may be applied, and electrical response signals may be detected, over a region of the body tissue larger than the area of the electrode array. Conversely, for a region of the body tissue of a given size, fewer electrodes can be deployed, which can reduce the complexity of electrical interconnections. Movement of the electrode array also enables electrical measurements with a fine resolution, using incremental positions of the electrodes more closely spaced than the physical spacing of the electrodes.

In another embodiment the electrode array and the ultrasound transducer may be mounted on a common element that is moveable with respect to the apparatus. This enables the complexity of electrical connections to the ultrasound transducer and the electrode array to be reduced, for example by using common routing for the connections.

The common element may be rotatable with respect to the apparatus. This feature enables the apparatus to be compact.

The electrode array may be substantially flat. This enables a simple design and manufacture. However, the electrode array need not be flat. For example the electrode array may be profiled to complement the contours of the body tissue.

The apparatus may comprise a container for receiving the body tissue, wherein the electrode array is provided at an inside bottom surface of the container. This enables the body tissue to be held in the container during the electrical impedance detection and ultrasound scanning, which can help to ensure that the body tissue is in an optimum position relative to the electrode array and the ultrasound transducer, and help to ensure that the body tissue remains stationary, resulting in improved resolution. It also enables the body tissue to be placed in a fluid, in particular an electrically conductive fluid, which can improve the electrical contact between the body tissue and the electrode array, enabling more reliable characterization.

The apparatus may comprise means for varying the depth of the container. This can assist placement of the body tissue in an optimum position relative to the electrode array and the ultrasound probe, and help to ensure that the body tissue is stationary during characterization, resulting in improved resolution. Furthermore, the signal propagation distance may be reduced, resulting in improved sensitivity of the apparatus in detecting signals.

The ultrasound probe may be moveable around a side wall of the container. In particular, the path of the ultrasound probe may be around a side wall of the container. This enables the first ultrasound signal to be applied to a different side or surface of the body tissue than the first electrical signal, which is advantageous in providing the electrical response signal and the ultrasound response signal relating to different planes or surfaces of the body tissue, which can assist detection and characterization of features of the body tissue. The ultrasound transducer may be mounted behind the electrode array. This enables the first electrical signal and the first ultrasound signal to be applied to the same side of the body tissue. Such an arrangement is advantageous in providing the electrical response signals and the ultrasound response signals relating to a common plane or surface of the body tissue. This also contributes to a high spatial correlation of the electrical response signals and the ultrasound response signals, which can assist detection and characterization of features of the body tissue.

The body tissue may be breast tissue. In this embodiment, the container may be dimensioned so as to receive a human or animal breast.

The apparatus may comprise a display for displaying an image representative of the electrical impedance detection based on the first output signal and an image representative of the ultrasound scanning based on the second output signal. Likewise, the method may comprise displaying an image representative of the electrical impedance detection based on the first output signal and an image representative of the ultrasound scanning based on the second output signal. In particular, the display may be arranged to display the image representative of the electrical impedance detection and the image representative of the ultrasound scanning simultaneously. Likewise, the method may comprise displaying the image representative of the electrical impedance detection and the image representative of the ultrasound scanning simultaneously. Furthermore, the apparatus may comprise a display for displaying an image representative of a combination of the electrical impedance detection and the ultrasound scanning. Likewise, the method may comprise displaying an image representative of a combination of the electrical impedance detection and the ultrasound scanning. Therefore, images representing the electrical response signal and ultrasound response signal may be generated having a high degree of spatial correlation, which can assist detection and characterization of features of the body tissue.

BRIEF DESCRIPTION

For a better understanding of various examples of embodiments of the present invention reference will now be made by way of example only to the accompanying drawings in which.

DETAILED DESCRIPTION

Figure 1:
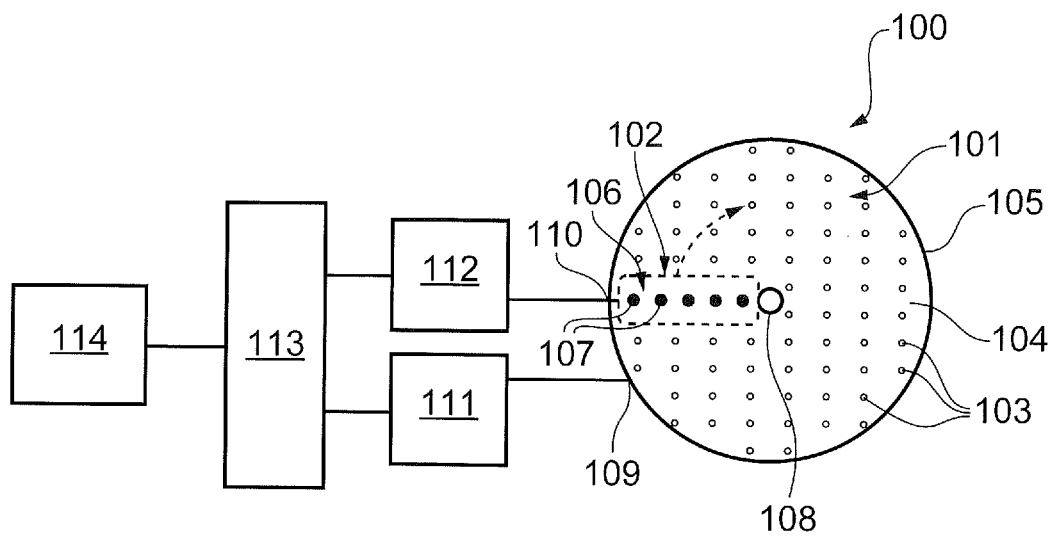
FIG. 1 is a schematic diagram of an apparatus for detecting signals characteristic of a body tissue.

Referring to FIG. 1, an apparatus 100 for detecting signals characteristic of body tissue comprises an electrode array 101 and an ultrasound probe 102.

The electrode array 101 comprises a plurality of electrodes 103 disposed on a face 104 of an electrode plate 105. In use, the body tissue (not illustrated) is placed over the electrode plate 105, adjacent to a face 104 of the electrode plate 105, either in contact with, or space apart from, the face 104. The electrodes 103 are able to apply a first electrical signal to the body tissue during electrical impedance measurements on the body tissue. The electrodes 103 are electrically coupled to a first controller 111 for transmitting the first electrical signal to the electrodes 103 for applying to the body tissue and for receiving a first output signal from electrodes 103, which first output signal depends on electrical response signals, characteristic of the body tissue, received at the electrodes 103.

The ultrasound probe 102 comprises a plurality of ultrasound transducers 107 disposed on a face 106 of the ultrasound probe 102. The ultrasound transducers 107 are able to apply a first ultrasound signal to the body tissue during ultrasound examination on the body tissue. The ultrasound transducers 107 are electrically coupled to a second controller 112 for providing a second input signal, generally in the form of electrical pulses, to the ultrasound transducers 107 that cause the ultrasound transducers 107 to apply the first ultrasound signal to the body tissue, and for receiving a second output signal from the ultrasound transducers 107, which second output signal depends on ultrasound response signals, characteristic of the body tissue, received at the ultrasound transducers 107.

The face 106 of the ultrasound probe 102 on which the ultrasound transducers 107 are disposed is adjacent to the electrode plate 105 and on the opposite side of the electrode plate 105 to the face 104 of the electrode plate 105 on which the electrodes 103 are disposed. Therefore, if the electrode plate 105 is placed horizontally with the face 104 of the electrode plate 105 on which the electrodes 103 are disposed upwards, then the ultrasound probe 102 is beneath the electrode plate 105 with the face 106 of the ultrasound probe 102 on which the ultrasound transducers 107 are disposed also upwards. Therefore, the ultrasound transducers 107 are arranged in a plane substantially parallel to the electrode plate 105. This enables the electrical signals and the ultrasound signals to be applied to the body tissue in directions that are substantially parallel to each other.

The ultrasound probe 102 and the electrode plate 105 are mechanically coupled, whereby the ultrasound probe 102 is rotatable about an axis 108 substantially perpendicular to the electrode plate 105. In particular, the axis 108 is coupled to, central to, and substantially perpendicular to the electrode plate 105. As the ultrasound probe 102 rotates, the path of each ultrasound transducer 107 traces an arc of a circle, and eventually a circular loop if the rotation continues for 360 degrees.

In one embodiment, the ultrasound probe 102 is rotatable relative to the electrode plate 105, whereas in another embodiment the electrode plate 105 also rotates, with the ultrasound probe 102, about the same axis 108. The mechanical arrangement for driving the rotation of ultrasound probe 102, and optionally the electrode plate 105, is omitted from FIG. 1 for clarity; a conventional drive mechanism may be used.

In the case that the ultrasound probe 102 is rotatable relative to the electrode plate 105, the ultrasound probe 102 passes across one face of the electrode plate 105 for sounding body tissue located adjacent the opposite side, face 104, of the electrode plate 105. As only one of the electrode plate 105 and the ultrasound transducer 107 need move, the mechanical drive arrangement may be simple. The electrode plate 105 is at least partially transparent to ultrasound signals. The greater the transparency of the electrode plate 105 to ultrasound signals, the greater the sensitivity of the apparatus 100 in detecting the ultrasound response signals.

Rotation of the ultrasound probe 102 enables an area to be sounded which is larger than the area of the ultrasound probe 102, whilst maintaining a high degree of temporal and spatial correlation of the ultrasound response signals and the electrical response signals. Therefore the ultrasound probe 102 may be compact and employ relatively few ultrasound transducers 107, which reduces the complexity of electrical interconnections and reduces the power required to drive the ultrasound transducers 107. Rotation also enables sounding with a fine resolution, using incremental positions of the ultrasound transducers 107 more closely spaced than the physical spacing of the ultrasound transducers 107.

Likewise, rotation of the electrode plate 105 enables the first electrical signals to be applied, and the electrical response signals to be detected, over a region of the body tissue larger than the area of the electrode plate 105 over which the electrodes 103 are deployed. Conversely, for a region of the body tissue of a given size, fewer electrodes 103 may be deployed, which can reduce the complexity of electrical connections.

Rotation of the electrode plate 105 also enables electrical measurements with a fine resolution, using incremental positions of the electrodes 103 more closely spaced than the physical spacing on the electrodes 103.

Because the electrode plate 105 and the ultrasound transducers 107 are mechanically linked by the axis 108 of rotation, the ultrasound transducers 107 and the electrodes 103 have a defined spatial relationship. In the case that the electrode plate 105 and the ultrasound probe 102 rotate together, the defined spatial relationship is a fixed relationship. In the case that the ultrasound probe 102 is rotatable relative to the electrode plate 105, the defined spatial relationship is a fixed path or trajectory. In either case, the path of the ultrasound probe 102 is fixed relative to a location of the electrode plate 105 at which the electrode plate 105 is used to perform the electrical impedance detection. Therefore, the electrical response signal and the ultrasound response signal can be ensured to have a defined relationship.

In the case that the ultrasound probe 102 is rotatable relative to the electrode plate 105, in use, the electrode plate 105 may be maintained in a constant position relative to the body tissue during rotation of the ultrasound probe 102, thereby providing a fixed reference position, which can contribute to high resolution characterization of the body tissue.

In the case that the electrode plate 105 and the ultrasound probe 102 rotate together, the complexity of electrical connections to the electrodes 104 and the ultrasound transducers 105 may be reduced, for example by using common routing for the connections.

The electrodes 103 are coupled to a first port 109, and the ultrasound transducers 107 are coupled to a second port 110. The first port 109 is bidirectional, for conveying signals to and from the electrodes 103. The second port 110 is also bidirectional, for conveying signals to and from the ultrasound transducers 107. For clarity, connections between the first port 109 and the electrodes 103, and between the second port 110 and the ultrasound transducers 107, are not illustrated in FIG. 1. These connections may, for example, be located on the face of the electrode plate 105 opposite to the face 104, or may be internal to the electrode plate 105.

There is a first controller 111 coupled to the first port 109. The first controller 111 generates the first input signal which is delivered via the first port 109 to one or more of the electrodes 103 where, in response to the first input signal, the first electrical signal is transmitted to the body tissue. The first electrical signal passes through the body tissue and is received at other of the electrodes 103. These received signals are termed electrical response signals in this specification and the accompanying claims. The first output signal, dependent on the electrical response signals is delivered to the first controller 111 via the first port 109.

There is a second controller 112 coupled to the second port 110. The second controller 112 generates the second input signal which is delivered via the second port 110 to the ultrasound transducers 107. The second input signal may be, for example an electrical signal or optical signal. The ultrasound transducers 107 convert the second input signal to the first ultrasound signal which is transmitted to the body tissue. The first ultrasound signal is reflected in the body tissue. These reflections are termed ultrasound response signals in this specification and the accompanying claims. The ultrasound response signals are detected by the ultrasound transducers 107, which convert the ultrasound response signals to the second output signal which is delivered to the second controller 112 via the second port 110.

The first and second controllers 111, 112 are coupled to a data generator 113. The data generator 113 generates electrical impedance data based on the first output signal, and ultrasound data based on the second output signal. The ultrasound data and the electrical impedance data are characteristic of the body tissue.

The data generator 113 is coupled to a display 114 for displaying simultaneously an image representative of the electrical impedance data and an image representative of the ultrasound data. Because of the known spatial relationship of the images, a person interpreting the images is able to make direct comparison of portions of the images that are known to relate to the same region of the body tissue.

Alternatively, the data generator 113 may combine the ultrasound data and the electrical impedance data, for example by correlation, and the display 114 may display an image representative of the combined ultrasound data and electrical impedance data. By this means, the electrical impedance data and the ultrasound data may be combined to provide an enhanced image, which can assist detection and characterization of features of the body tissue. Features of the body tissue that may not be apparent from solely the electrical impedance data or the ultrasound data may become apparent after the correlation of the electrical impedance data and the ultrasound data. The images may be two or three dimensional.

Figure 2:
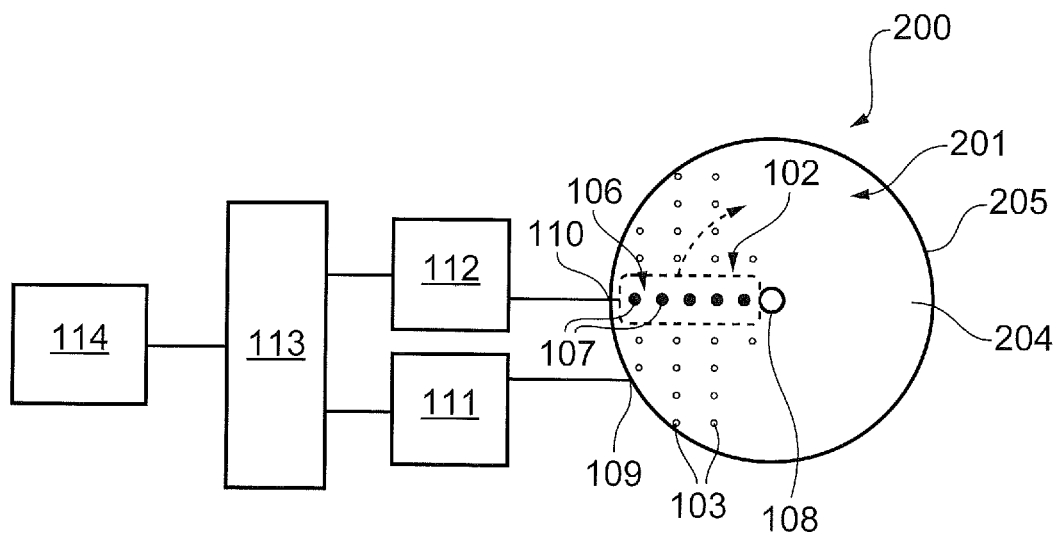
FIG. 2 is a schematic diagram of an apparatus for detecting signals characteristic of a body tissue.

Referring to FIG. 2, an apparatus 200 comprises an electrode plate 205 having a reduced number of electrodes 103 compared with the electrode plate 105 illustrated in FIG. 1. The electrodes 103 are deployed across a segment of a face 204 of the electrode plate 205. Such an arrangement may be used in conjunction with an electrode plate 205 that rotates as described above, in which case the path of the electrodes 103 will trace an arc or full circle. All other elements of FIG. 2 are identical to elements of FIG. 1 and have identical reference numerals to those respective elements.

Figure 3:
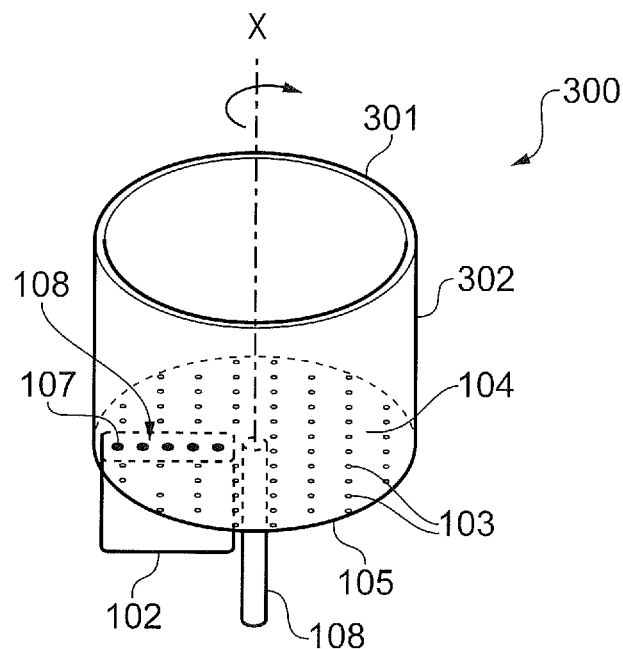
FIG. 3 is a schematic three dimensional schematic view of an apparatus for detecting signals characteristic of a body tissue.

Referring to FIG. 3, there is illustrated a three dimensional schematic view of an apparatus 300 comprising the electrode plate 105 and the ultrasound probe 102 of FIG. 1, in which additionally there is a container 301 for receiving the body tissue. For example, the container 301 may be dimensioned for receiving a breast. The container 301 has a side wall 302. The electrode plate 105 forms the base of the container 301, with the face 104 being inside the container 301. The position of the electrode plate 105 within the container 301 may be varied, in order to vary the volume of the container 301 available for receiving the body tissue. The ultrasound probe 102 is beneath the container 301, with its face 106 adjacent to the lower face of the electrode plate 105. The ultrasound probe 102, and optionally the container 301 including the electrode plate 105, rotates about the axis 108. The line of the axis 108 is denoted by the dashed line X. In use, the container 301 may contain fluid for enhancing the transmission of ultrasound and/or electrical signals. For clarity the first and second ports 109, 110, the first and second controllers 111, 112, the data generator 113 and the display 114 are omitted from FIGS. 3 and 4, but are identical to the corresponding elements of FIG. 1.

Figure 4:
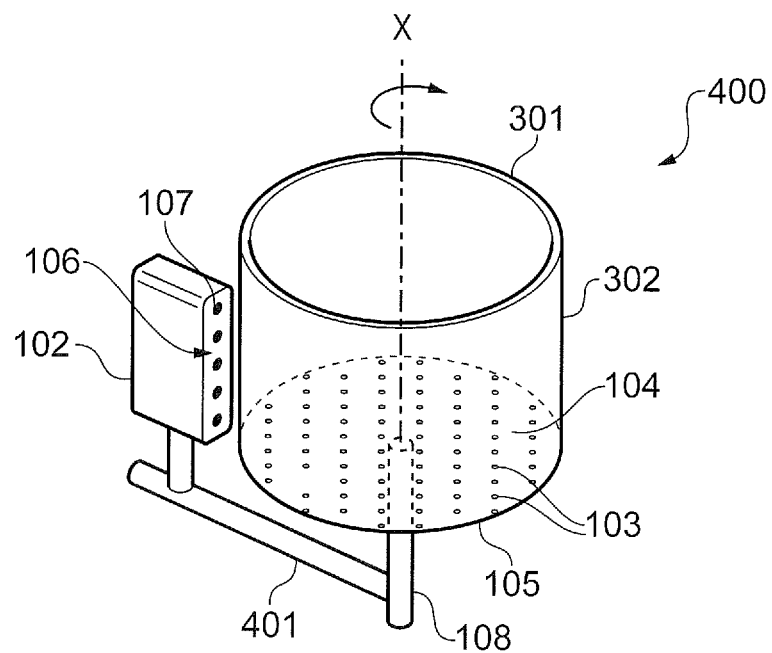
FIG. 4 is a schematic three dimensional schematic view of an apparatus for detecting signals characteristic of a body tissue.

Referring to FIG. 4, there is illustrated a three dimensional schematic view of an apparatus 400 comprising the ultrasound probe 102, the electrode plate 105 and the container 301, in which the electrode plate 105 forms the base of the container 301, with the face 104 being inside the container 301. The ultrasound probe 102 is beside the container 301, with the face 106 of the ultrasound probe 102 adjacent the side wall 302 of the container 301. The side wall 302 is vertical and the face 106 of the ultrasound probe 102 is also vertical. Therefore, the ultrasound transducers 107 are arranged vertically. In this embodiment, the ultrasound transducers 107 are arranged in a plane substantially perpendicular to the plane of the electrode plate 105. In use, the ultrasound probe 102 passes externally across the side wall 302 of the container 301, and the side wall 302 comprises a material which is at least partially transparent to ultrasound signals.

There is a mechanical linkage 401 coupling the ultrasound probe 102 to the axis 108 and therefore to the electrode plate 105. The ultrasound probe 102, and optionally the container 301 including the electrode plate 105, rotates about the axis 108. The line of the axis is denoted by the dashed line X. In this way, the first ultrasound signal may be applied to the body tissue in the container 301 through the side wall 302, and the first electrical signal may be applied to the body tissue by means of the electrodes 103 in the electrode plate 105 forming the base of the container 301. Thus, the first ultrasound signal and the first electrical signal may be applied to the body tissue in planes that are substantially perpendicular to each other.

Because the electrode plate 105 and the ultrasound probe 102 in the embodiment of FIG. 4 are mechanically linked by the mechanical linkage 401 and the axis 108, the ultrasound transducers 107 and the electrodes 103 have a defined spatial relationship, which is either a fixed relationship, if the ultrasound probe 102 and the electrode plate 105 rotate together, or a fixed path or trajectory if the ultrasound probe 102 rotates relative to the electrode plate 105. Therefore, the electrical response signals and the ultrasound response signals can be ensured to have a defined relationship.

In the embodiments described with reference to FIGS. 3 and 4, the container 301 is cylindrical. Containers of other shapes may be used. For example, a container may be used which has sides that taper outwards away from the electrode plate 105. In this case the face 106 of the ultrasound probe 102 need not be vertical but may be substantially parallel to the tapered sides, such that the ultrasound transducers 107 are arranged in a plane at an angle greater than zero degrees and less than ninety degree to the plane of the electrode plate 105.

As another example, a container may be used which has sides that are curved. In this way the shape of the container may be contoured in a similar shape to the body tissue. The face 106 of the ultrasound probe 102, and the arrangement of ultrasound transducers 107 may be profiled to complement the shape of the sides of the container.

Such shaping of the container 301 and arrangements of the ultrasound transducers 107 enables the first electrical signal and the first ultrasound signal to be applied to different sides or surfaces of the body tissue, and can be advantageous in providing the first and second output signals relating to different projections of a common region of the body tissue, enabling the characterization of the body tissue to be determined with increased resolution, and is particularly advantageous for three dimensional characterization of the body tissue.

Similarly, although the electrode plate 105 illustrated in FIGS. 1 to 4 is flat, this is not an essential feature, and the electrode plate 105, or at least the face 104, may be non-flat. For example, the face 104 may be profiled in a similar shape to the body tissue. This enables distortion of the shape of the body tissue to be reduced or avoided. The face 106 of the ultrasound probe 102, and the arrangement of ultrasound transducers 107 may be profiled to complement the shape of the adjacent electrode plate 105.

By employing shapes which are complementary to the shape of the body tissue, the length of the signal path between the electrode plate 105 and the body tissue, and between the ultrasound transducers 107 and the body tissue, may be reduced, resulting in improved sensitivity of the apparatus in detecting the response signals In the embodiments illustrated in FIGS. 1 to 4 the electrode plate 105 is circular. This is not an essential feature, and other shapes may be used.

Furthermore, the axis 108 need not be located at the center of the electrode plate 105. Also, the axis 108 may be located asymmetrically with respect to the ultrasound probe 102, and in particular with respect to the arrangement of ultrasound transducers 107. The greater the asymmetry, the greater the radius of the arc which the ultrasound transducers 107 may trace.

The signals delivered via the first port 109 and the second port 110 may be electric currents or voltages, or may be optical signals. Also, they may be analogue or digital signals. Where optical signals are used, conversion between optical and electrical signals may be performed by the ultrasound transducers 107, by the electrodes 103 and by the first and second controllers 111, 112. Digital to analogue conversion, and analogue to digital conversion, may be performed by the ultrasound transducers 107, by the electrodes 103 and by the first and second controllers 111, 112. The ultrasound transducers 107, the electrodes 103 and the first and second controllers 111, 112 may include signal processing, for example amplification and filtering. The first controller 111 may be integral with the electrode plate 105 and the second controller 112 may be integral with the ultrasound probe 102, in which case either or both of the first and second ports 109, 110 may be internal to the electrode plate 105 or ultrasound probe 102 respectively. Alternatively the first controller 111 may be spaced apart from the electrode plate 105 by means of cables, and/or the second controller 112 may be spaced apart from the ultrasound probe 102 by means of cables.

The first controller 111 and the second controller 112 may be coupled, and indeed may be a common controller. This enables the generation of the first and second signals to be synchronized. For example, the relative timing and/or the magnitude of the first and second signals may be controlled.

The features of the embodiments of FIGS. 3 and 4 may be combined, by providing an ultrasound probe 102 that has a part beneath the electrode plate 105 as in FIG. 3 and a part beside the container 301 as in FIG. 4. This arrangement enables more detailed evaluation of body tissue characteristics.

From reading the present disclosure, other variations and modifications will be apparent to the skilled person. Such variations and modifications may involve equivalent and other features which are known in the art of electrical impedance imaging and ultrasound techniques for medical diagnostics, and which may be used instead of, or in addition to, features described herein.

Although the appended claims are directed to particular combinations of features, it should be understood that the scope of the disclosure of embodiments of the present invention also includes any novel feature or any novel combination of features disclosed herein either explicitly or implicitly or any generalization thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub combination.

For the sake of completeness it is also stated that the term "comprising" does not exclude other elements or steps, the term "a" or "an" does not exclude a plurality.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

I claim:

1. An apparatus for performing electrical impedance detection and ultrasound scanning of body tissue, the apparatus comprising:
   an electrode array configured to perform electrical impedance detection, the electrode array being configured to apply a first electrical signal to the body tissue, to receive an electrical response signal characteristic of the body tissue, and to provide a first output signal representative of the electrical response signal; and
   an ultrasound transducer configured to perform ultrasound scanning, the ultrasound scanner being configured to apply a first ultrasound signal to the body tissue, to receive an ultrasound response signal characteristic of the body tissue, and to provide a second output signal representative of the ultrasound response signal, wherein the ultrasound transducer is mounted so as to be moveable during performance of the ultrasound scanning when the ultrasound transducer is used to receive the ultrasound response signal, along a path that is fixed relative to a location of the electrode array when the electrode array is used to receive the electrical response signal.

2. An apparatus as claimed in claim 1, wherein the ultrasound transducer is mounted for predetermined movement, about an axis, during each ultrasound scan to produce an image.

3. An apparatus as claimed in claim 1, wherein the ultrasound transducer is mounted so as to be moveable with respect to the electrode array during performance of the ultrasound scanning.

4. An apparatus as claimed in claim 1, wherein the ultrasound transducer and the electrode array are mounted on a common element that is moveable with respect to the apparatus.

5. An apparatus as claimed in claim 4, wherein the common element is rotatable with respect to the apparatus.

6. An apparatus as claimed in claim 1, comprising a container for receiving the body tissue, wherein the electrode array is provided at an inside bottom surface of the container, and wherein a depth of the container is variable, wherein the ultrasound transducer is moveable with respect to the container.

7. An apparatus as claimed in claim 1, wherein the ultrasound transducer is mounted behind the electrode array.

8. An apparatus as claimed in claim 1, comprising a display for displaying an image representative of the electrical impedance detection based on the received electrical response signal and an image representative of the ultrasound scanning based on the received ultrasound response signal, wherein the display is arranged to display the image representative of the electrical impedance detection and the image representative of the ultrasound scanning simultaneously, wherein the ultrasound transducer and the electrode array have a spatial relationship defined by the path that defines a relationship between the received electrical response signal and the received ultrasound response signal such that the image based on the received electrical response signal and the image based on the received ultrasound response signal have a defined spatial relationship.

9. An apparatus as claimed in claim 1, comprising a container for receiving the body tissue and an electrically conductive fluid, wherein the combination of the container and electrically conductive fluid spaces the body tissue from the electrode array and wherein the electrically conductive fluid provides electrical contact between the electrode array and the body tissue.

10. An apparatus as claimed in claim 1, wherein the electrode array is an array of a plurality of spaced electrodes controlled to provide first electrical signals to the body tissue via different pairs of the plurality of electrodes and controlled to receive electrical response signals, in response, from other electrodes of the plurality of spaced electrodes.

11. An apparatus as claimed in claim 1, wherein the ultrasound transducer is moveable during ultrasound scanning with respect to the apparatus along the path that is fixed relative to a location of the electrode array at which the electrode array is arranged to perform the electrical impedance detection and wherein the ultrasound transducer is mechanically linked to rotate about an axis substantially perpendicular to the electrode array to trace at least an arc of a circle.

12. An apparatus as claimed in claim 1, wherein the ultrasound transducer is mounted for predetermined movement, about an axis, during each ultrasound scan to produce an image.

13. A method of performing electrical impedance detection and ultrasound scanning of body tissue simultaneously, the method comprising:

performing electrical impedance detection with an electrode array by applying a first electrical signal to the body tissue, receiving an electrical response signal characteristic of the body tissue, and providing a first output signal representative of the electrical response signal; and while performing electrical impedance detection, moving an ultrasound transducer and performing ultrasound scanning with the moving ultrasound transducer by applying a first ultrasound signal to the body tissue, receiving an ultrasound response signal characteristic of the body tissue, and providing a second output signal representative of the ultrasound response signal.

14. A method as claimed in claim 13, wherein during the performing of the ultrasound scanning the ultrasound transducer is moved along a fixed path.

15. A method as claimed in claim 13, wherein the ultrasound transducer is moved with respect to the electrode array during the performing of the ultrasound scanning.

16. A method as claimed in claim 13, wherein the ultrasound transducer is moved with the electrode array during the performing of the ultrasound scanning.

17. A method as claimed in claim 13, comprising displaying an image representative of the electrical impedance detection based on the first output signal and an image representative of the ultrasound scanning based on the second output signal.

18. A method as claimed in claim 13, wherein a container receives the body tissue and an electrically conductive fluid, wherein the combination of the container and electrically conductive fluid spaces the body tissue from the electrode array and wherein the electrically conductive fluid provides electrical contact between the electrode array and the body tissue.

19. A method as claimed in claim 13, wherein the electrode array is an array of a plurality of spaced electrodes controlled to provide first electrical signals to the body tissue via different pairs of the plurality of electrodes and controlled to receive electrical response signals, in response, from other electrodes of the plurality of spaced electrodes.

20. An apparatus for performing electrical impedance detection and ultrasound scanning of body tissue, the apparatus comprising:

an electrode array configured to perform electrical impedance detection, the electrode array being configured to apply a first electrical signal to the body tissue, to receive an electrical response signal characteristic of the body tissue, and to provide a first output signal representative of the electrical response signal; and an ultrasound transducer configured to perform ultrasound scanning, the ultrasound scanner being configured to apply a first ultrasound signal to the body tissue, to receive an ultrasound response signal characteristic of the body tissue, and to provide a second output signal representative of the ultrasound response signal, wherein the ultrasound transducer is mounted so as to be moveable, during performance of the ultrasound scanning when the ultrasound transducer is used to receive the ultrasound response signal, along a path that is fixed relative to a location of the electrode array, when the electrode array is used to receive the electrical response signal to achieve temporal and spatial correlation of the ultrasound response signal and the electrical response signal.

* * * * *